(12) United States Patent
Mark (10) Patent No.: US 8,066,648 B1
(45) Date of Patent: Nov. 29, 2011

(54) FLUID CONNECTOR AND BIOPSY SYSTEM INCLUDING SAME

(75) Inventor: Joseph L. Mark, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 664 days.

(21) Appl. No.: 10/786,727

(22) Filed: Feb. 25, 2004

(51) Int. Cl.
*A61B 10/00* (2006.01)

(52) U.S. Cl. ......... 600/566; 600/562; 600/564; 600/565

(58) Field of Classification Search .......... 600/562–566, 600/571, 300, 560, 561, 573, 576, 577, 578, 600/579, 101, 131; 604/284
See application file for complete search history.

(56) References Cited

U.S. PATENT DOCUMENTS

| | | | | |
|---|---|---|---|---|
| 2,866,457 A | * | 12/1958 | Moore | 604/83 |
| 3,844,272 A | * | 10/1974 | Banko | 600/566 |
| 4,598,698 A | * | 7/1986 | Siegmund | 600/131 |
| 5,335,671 A | * | 8/1994 | Clement | 600/566 |
| 5,403,276 A | * | 4/1995 | Schechter et al. | 604/22 |
| 5,505,210 A | * | 4/1996 | Clement | 600/566 |
| 5,868,785 A | * | 2/1999 | Tal et al. | 606/207 |
| 6,162,187 A | * | 12/2000 | Buzzard et al. | 600/573 |
| 6,197,005 B1 | * | 3/2001 | Gerlach et al. | 604/247 |
| 6,273,862 B1 | * | 8/2001 | Privitera et al. | 600/568 |
| 6,331,165 B1 | * | 12/2001 | Turturro et al. | 600/562 |
| 2002/0082519 A1 | * | 6/2002 | Miller et al. | 600/566 |

* cited by examiner

*Primary Examiner* — Jeffrey G Hoekstra
(74) *Attorney, Agent, or Firm* — Rader, Fishman & Grauer, PLLC (57) ABSTRACT

A fluid connector is provided for a biopsy system that includes a vacuum assisted biopsy device, a first fluid source and a second fluid source. In an embodiment, the fluid connector includes a body member having a first input port, a second input port and an output port. The first input port includes a first check valve in fluid communication with the first fluid source, the second input port includes a second check valve in fluid communication with the second fluid source and the output port is provided in communication with the vacuum assisted biopsy device. A biopsy system including a fluid connector of the present invention is also provided.

23 Claims, 6 Drawing Sheets

FLUID CONNECTOR AND BIOPSY SYSTEM INCLUDING SAME

BACKGROUND OF THE INVENTION

1. Field of the Invention

The present invention relates to biopsy instruments and methods for taking a biopsy. Particularly, this invention relates to a fluid connector and biopsy system including a fluid connector for introducing fluids into a patient during a biopsy procedure.

2. Description of the Related Art

In the diagnosis and treatment of cancer, it is often necessary to remove multiple tissue samples from a suspicious mass. Prior to removal, the suspicious mass is generally evaluated by taking a biopsy to determine if the mass is malignant or benign. Early diagnosis of various forms of cancer, such as breast cancer for example, may prevent the spread of the disease to other parts of the body.

An exemplary vacuum assisted biopsy apparatus is disclosed in U.S. Pat. No. 6,638,235. The exemplary biopsy apparatus is a minimally invasive biopsy instrument. Unlike the biopsy apparatus before it, the exemplary apparatus includes a lightweight, pneumatically controlled hand-piece having a non-clogging and non-occluding cutting blade design. A unique tissue collection system is used to aid in capture, location, identification and staging of the biopsy sample, and retains histological and pathological viability of the removed tissue without exposing the medical staff to the patient's body fluids. To facilitate tissue removal, the exemplary biopsy apparatus is also configured to introduce, among other fluids, a saline solution to the surgical site during a biopsy procedure. In one embodiment of the design, the saline solution is contained in a sealed bag that includes a fluid supply line communicating the sealed bag with the cutting portion of the biopsy device. A pinch valve is used to crimp the fluid supply line to selectively interrupt the flow of saline solution to the surgical site.

Although the exemplary biopsy apparatus disclosed in U.S. Pat. No. 6,638,235 represents a significant advancement in the field of medical biopsy, the introduction of fluids other than saline solution, such as anesthetics and haemostatic agents, requires that the fluid supply line be "broken" and the secondary fluid injected into the fluid supply line. Among other limitations, breaking the fluid supply line exposes the medical staff to the patient's body fluids. Additionally, breaking the fluid supply line to inject a second fluid adds additional time to the biopsy procedure. Therefore, a need exists for an improved biopsy system that incorporates the advancements of the exemplary biopsy apparatus described above into a fully sealed and efficiently operated biopsy system.

SUMMARY OF THE INVENTION

A fluid connector is provided for a biopsy system that includes a vacuum assisted biopsy device, a first fluid source and a second fluid source. In an embodiment, the fluid connector includes a body member having a first input port, a second input port and an output port. The first input port includes a first check valve in fluid communication with the first fluid source, the second input port includes a second check valve in fluid communication with the second fluid source and the output port is provided in communication with the vacuum assisted biopsy device. A biopsy system including a fluid connector of the present invention is also provided.

Among other features, the present invention allows two or more fluids to be introduced into the biopsy system without "breaking" any fluid lines connecting the first and second fluid sources to the biopsy device. Further, the fluid connector of the present invention allows two or more fluids to be introduced into the biopsy system without sacrificing any functionality of the traditional pinch valve design. Moreover, the fluid connector of the present invention allows automatic introduction of a fluid in the biopsy system as the vacuum assisted biopsy device is operated, thereby reducing the duration of the biopsy procedure.

BRIEF DESCRIPTION OF THE DRAWINGS

Embodiments of the invention will now be described, by way of example, with reference to the accompanying drawings, wherein.

DETAILED DESCRIPTION OF THE INVENTION

Referring now to the drawings, the preferred illustrative embodiments of the present invention are shown in detail. Although the drawings represent some preferred embodiments of the present invention, the drawings are not necessarily to scale and certain features may be exaggerated to better illustrate and explain the present invention. Further, the embodiments set forth herein are not intended to be exhaustive or otherwise limit or restrict the invention to the precise forms and configurations shown in the drawings and disclosed in the following detailed description.

Figure 1:
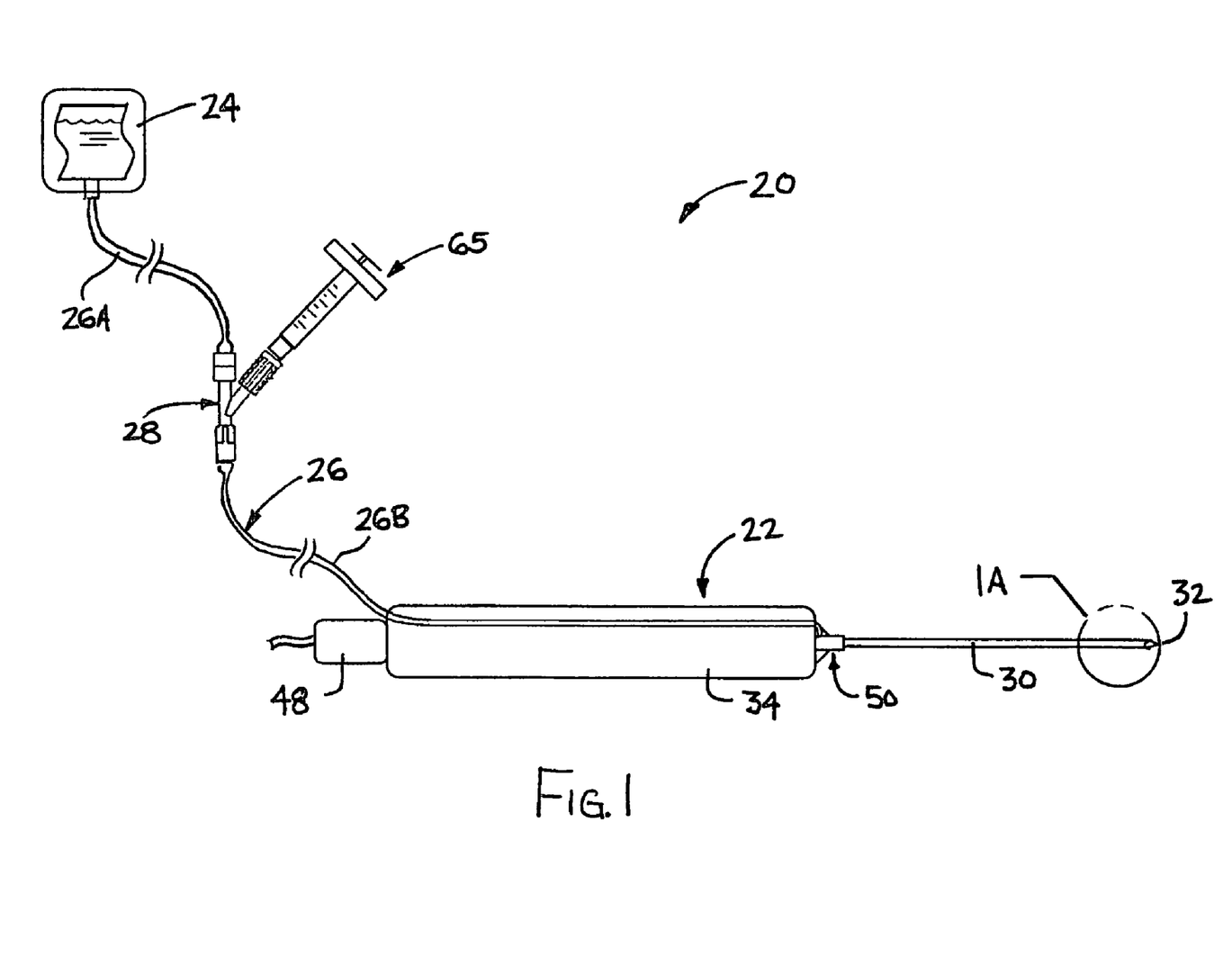
FIG. 1 is a schematic view of a biopsy system including a fluid connector according to an embodiment of the present invention.

A biopsy system 20 in accordance with an embodiment of the present invention is shown in FIG. 1. In the illustrated embodiment, biopsy system 20 includes a biopsy device 22, a first fluid source 24 containing a fluid, such as a isotonic solution, and a fluid conduit 26 connecting the biopsy device 22 to first fluid source 24. Biopsy system 20 also includes a fluid connector 28 positioned between two sections (26A, 26B) of fluid conduit 26 to provide biopsy device 22 in communication with first fluid source 24.

The present invention concerns a system for excising one or more tissue samples during a biopsy procedure, such as a biopsy of a human breast. Therefore, biopsy device 22 is configured for ease of use in the surgical environment. In the illustrated embodiment, biopsy device 22 is configured as a hand-held device. However, the same inventive principles may be employed in a biopsy device that is used stereotactically, wherein the biopsy device 22 is mounted in a support fixture that is used to position biopsy device 22 relative to the tissue to be sampled.

In an embodiment, biopsy device 22 is configured as a "tube-within-a-tube" cutting device. Specifically, biopsy device 22 includes an outer cannula 30 terminating in a tip 32. In a particular configuration, tip 32 is a trocar tip that may be used to penetrate a patient's skin. Alternatively, tip 32 may simply operate as a closure for an open end of outer cannula 30. In this instance, a separate introducer may be required for entering the patient.

Figure 1A:
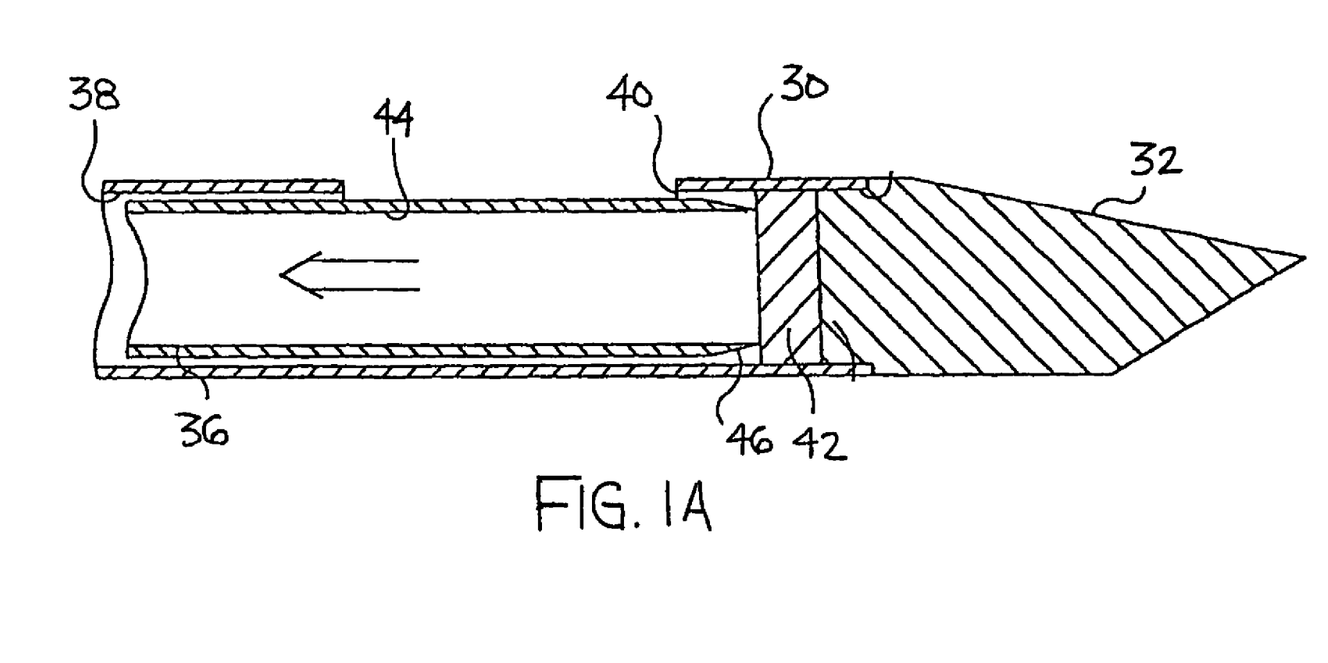
FIG. 1A is an enlarged detail view of a vacuum assisted biopsy device shown in FIG. 1.
Figure 2:
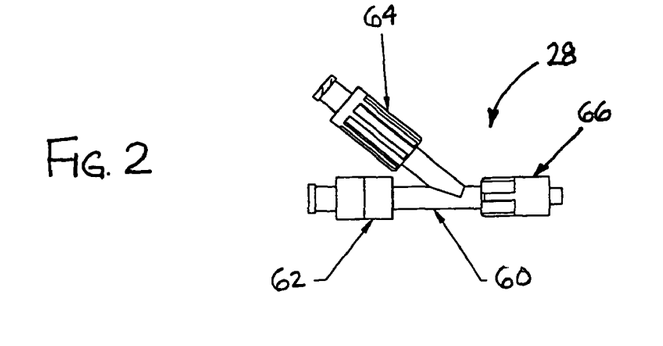
FIG. 2 is a front elevation view of a fluid connector according to an embodiment of the present invention.
Figure 3:
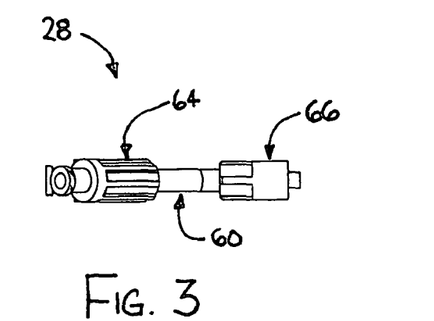
FIG. 3 is a top elevation view of the fluid connector of FIG. 2.
Figure 4:
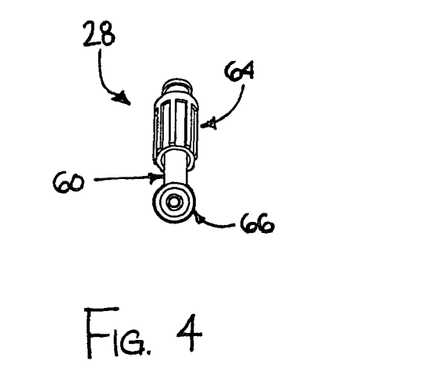
FIG. 4 is a left side elevation view of the fluid connector of FIG. 2.
Figure 5:
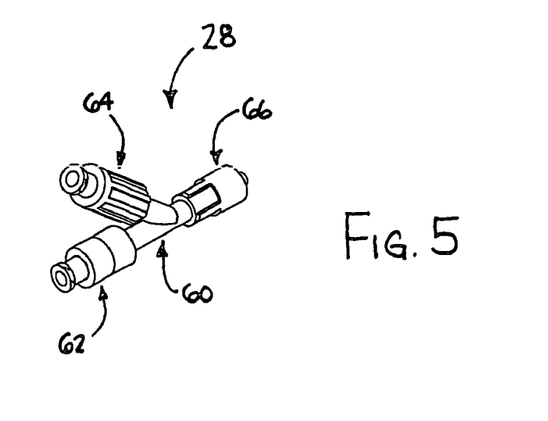
FIG. 5 is a perspective view of the fluid connector of FIG. 2.
Figure 6:
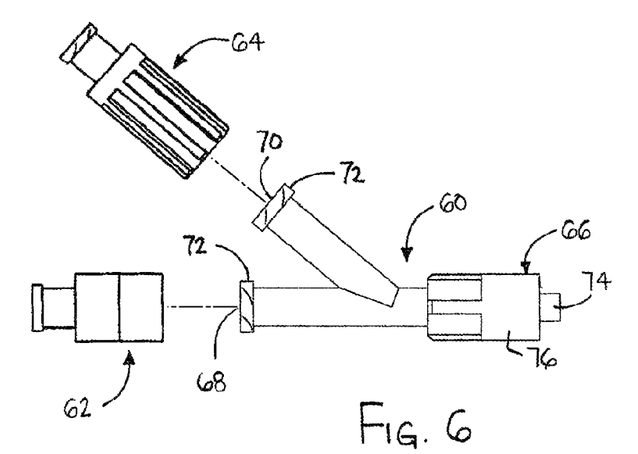
FIG. 6 is a front elevation view of a body member according to an embodiment of the present invention, for use in the fluid connector of FIG. 2.
Figure 7:
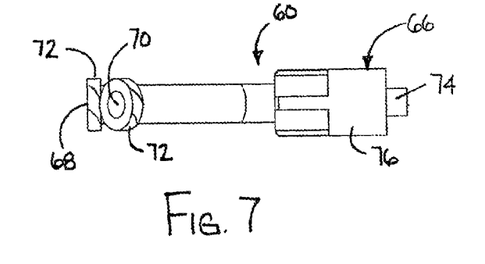
FIG. 7 is a top elevation view of the body member of FIG. 6.
Figure 8:
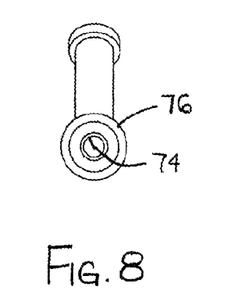
FIG. 8 is a left side elevation view of the body member of FIG. 6.
Figure 9:
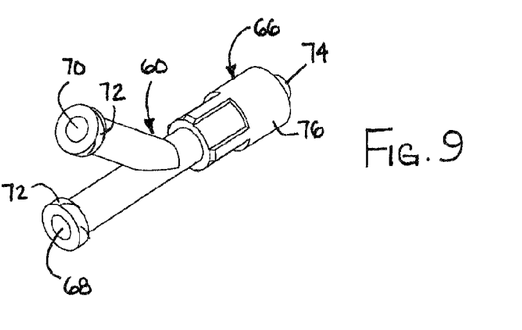
FIG. 9 is a perspective view of the body member of FIG. 6.
Figure 10:
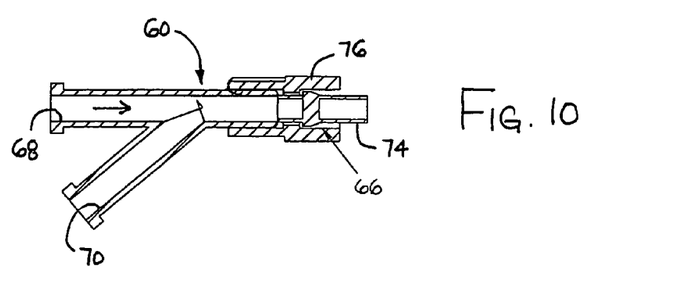
FIG. 10 is a cross-sectional view of the body member of FIG. 6.

In the illustrated embodiment, biopsy device 22 also includes a disposable housing 34 and an inner cannula 36 that fits concentrically within an outer lumen 38 of outer cannula 30 (see FIG. 1A). Outer cannula 30 defines a tissue-receiving opening 40 that communicates with outer lumen 38. The length of tissue receiving opening 40 generally determines the length of the biopsy sample or "core" extracted from the patient. Outer cannula 30 may also include a cutting board 42 that is at least snugly disposed within outer lumen 38 at the distal end of outer cannula 30.

Inner cannula 36 is at least partially supported by housing 34 or a component within housing 34 for sliding and rotational movement therein. In a particular implementation of biopsy device 22, inner cannula is slidingly and rotationally driven by pneumatically operated motors; however, the present invention is not limited thereto.

In the embodiment shown in FIG. 1A, inner cannula 36 defines an inner lumen 44 that is hollow along its entire length to provide for aspiration of the biopsy sample or "core". Inner cannula 36 terminates in a cutting edge 46 that may be formed by an inwardly beveled surface to provide a razor-sharp edge. Since inner cannula 36 provides an avenue for aspiration of a biopsy sample, the invention further contemplates the use of a vacuum source ("not shown") for pulling a biopsy sample through the inner cannula 36. In a particular configuration, the vacuum draws a tissue sample excised at the working end of inner cannula 36, and accompanying fluids, all the way through inner cannula 36 until it is deposited in a collection trap 48 (FIG. 1).

Outer cannula 30 is supported by a hub 50 mounted to the distal end of housing 34. In an embodiment, hub 50 is connected to fluid conduit section 26B and is configured to introduce fluids into outer lumen 38. Hub 50 thus provides a mechanism for introducing specific fluids contained in first fluid source 24 to the biopsy site. In certain procedures, it may be necessary to introduce additional fluids to the sampling site, such as an anesthetic or a haemostatic agent, which can be readily accommodated by fluid connector 28, as will be described below. Further features of biopsy device 22 and operation thereof are described in U.S. Pat. No. 6,638,235, which is owned by the Assignee of the present invention and is incorporated by reference herein in its entirety.

Referring to FIGS. 2-16, a fluid connector 28 according to an embodiment of the present invention is provided. In an embodiment, fluid connector 28 includes a generally Y-shaped body member 60 that includes a first check valve 62 provided in communication with fluid source 24 by first fluid conduit section 26A, a second check valve 64 adapted to interface with a second fluid source 65 (see FIG. 1), such as a needleless syringe, and an outlet port 66 provided in communication with biopsy device 22 by the second fluid conduit section 26B.

As shown in FIGS. 6-10, body member 60 includes a first inlet port 68 adapted to mate with first check valve 62 and a second inlet port 70 adapted to mate with second check valve 64. In an embodiment, first and second inlet ports 68, 70 are configured as a female luer fitting that includes a threaded surface 72. Outlet port 66 is configured as a male luer fitting having a flanged tubular portion 74 and an internally threaded cap 76 secured to body member 60. Outlet port 66 is adapted to mate with a corresponding female luer fitting (not shown) on second fluid conduit section 26B. While the luer style fitting configuration described above allows the components to be easily connected and provides a fluid-tight seal, other fitting styles and configurations are also within the scope of the present invention. Moreover, at least a portion of first and second check valves 62, 64 may be made integral with first and second inlet ports 68 and 70, respectively.

Figure 11:
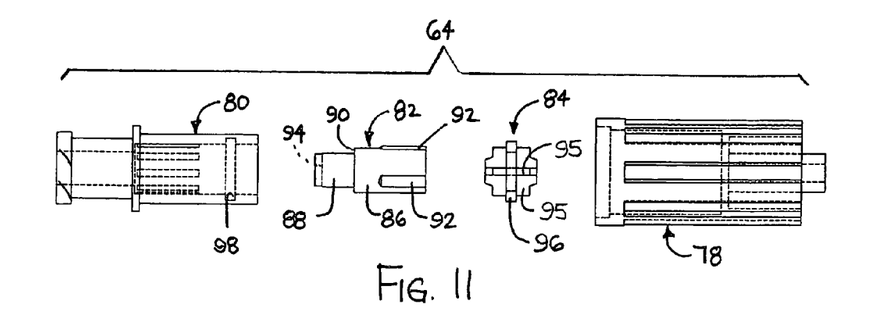
FIG. 11 is an exploded elevation view of an embodiment of a first check valve for use in the fluid connector of FIG. 2.
Figure 12:
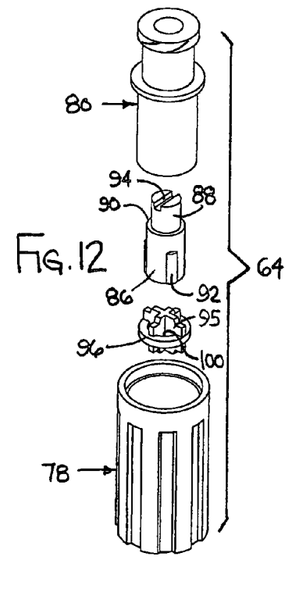
FIG. 12 is an exploded perspective view of the check valve of FIG. 11.
Figure 13:
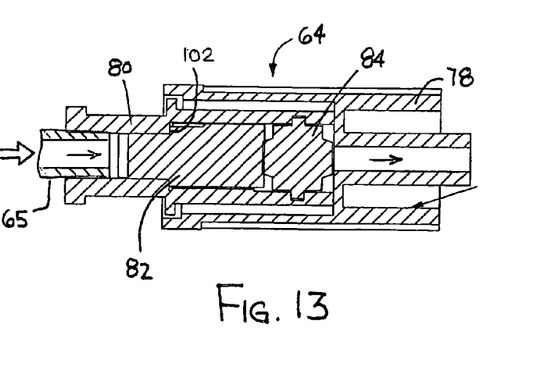
FIG. 13 is an assembled cross-sectional view of the check valve of FIG. 11.

Referring to FIGS. 11-13, an embodiment of second check valve 64 is shown. In the illustrated embodiment, second check valve 64 includes a first body portion 78, a second body portion 80 at least partially received in first body portion 78, a flexible valve member 82 and a valve seat 84. Flexible valve member 82, which may be made of a medical grade rubber or other resiliently flexible polymer, is generally cylindrical in shape and includes a base 86 and a reduced diameter engagement end 88 that defines a shoulder 90 on base 86. Base 86 also includes a plurality of fins 92 that project radially outwardly from base 86 and engage an inner wall of second body portion 80 when received therein. The space between fins 92 is sized to allow fluid to flow between base 86 and the inner wall of second body portion 80 when valve member 82 is compressed. Engagement end 88 may also include a channel 94 that allows the fluid to flow from secondary fluid source 65 into the space between fins 92 and second body portion 80 when valve member 82 is compressed.

In an embodiment, valve member 82 is retained within second body portion 80 by valve seat 84. Valve seat 84 includes a number of support members 95, which are shown as being generally orthogonal to one another in the embodiment of FIGS. 11-13. Support members 95 are surrounded by an annular locking ring 96 that is secured to support members 95 and sized to be received in an inwardly directed annular groove 98 in second body portion 80, as shown in FIG. 13. Locking ring 96 and the intersection of each support member 95 define a void 100 through which fluid is free to flow once it passes valve member 82. In the illustrated embodiment, valve seat 84 includes four (4) voids 100.

During assembly, valve member 82 is inserted into second body portion 80 followed by valve seat 84, which is then snapped into groove 98. Second body portion 80 is then inserted into first body portion 78 and secured therein, for example, by a pair of mating threads (not shown), gluing the components together or by any other suitable method. It will be appreciated that second check valve 64 is not limited to the embodiment shown in FIGS. 11-13 and that modifications to the illustrated design are within the scope of the invention.

In the illustrated embodiment, first body portion 78 includes a male luer fitting adapted to mate with a corresponding female luer fitting on second inlet port 70 of body member 60. Similarly, second body portion 80 includes a female luer fitting adapted to mate with a male luer fitting on secondary fluid source 65. While a luer style fitting configuration allows the components to be easily connected and also provides a fluid-tight seal, other fluid-tight fitting styles and configurations are within the scope of the present invention.

In operation, when second check valve 64 is closed, shoulder 90 of valve member 82 engages an inner surface 102 of second body member 80 to form a fluid-tight seal. The force required to unseat shoulder 90 from second body member 80 is generally, but not necessarily, greater than any force created by the aspirating pressure or vacuum in system 20 during operation of biopsy device 22. When it is desired to introduce a second fluid into biopsy system 20, second fluid source 65 is secured to second check valve 64 such that a portion of second fluid source 65 compresses valve member 82. Particularly, when second fluid source 65 includes a male luer fitting, a portion of the male luer fitting will compress valve member 82, as indicated in FIG. 13. Once valve member 82 is compressed to a point where channel 94 passes inner surface 102, fluid from second fluid source 65 is free to flow between fins 92, through voids 100 and into body member 60.

Figure 14:
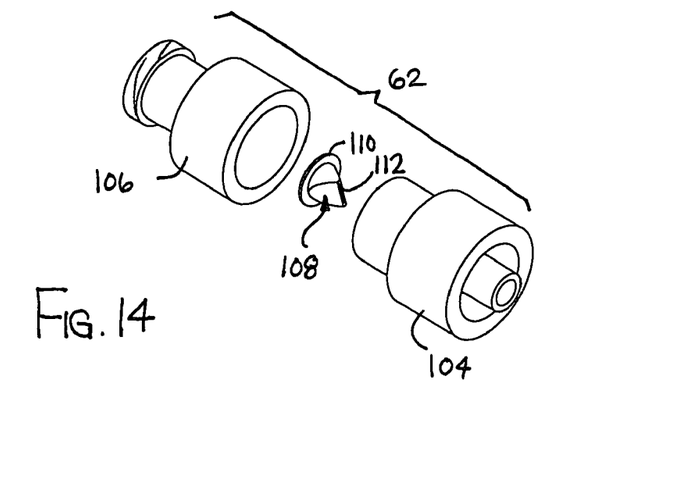
FIG. 14 is an exploded perspective view of an embodiment of a second check valve for use in the fluid connector of FIG. 2.
Figure 15:
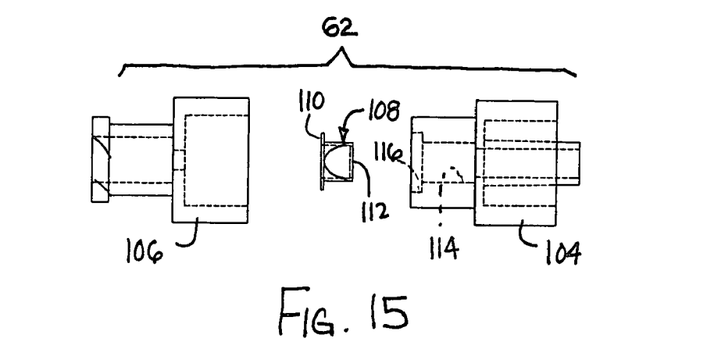
FIG. 15 is an exploded elevation view of the second check valve of FIG. 14.
Figure 16:
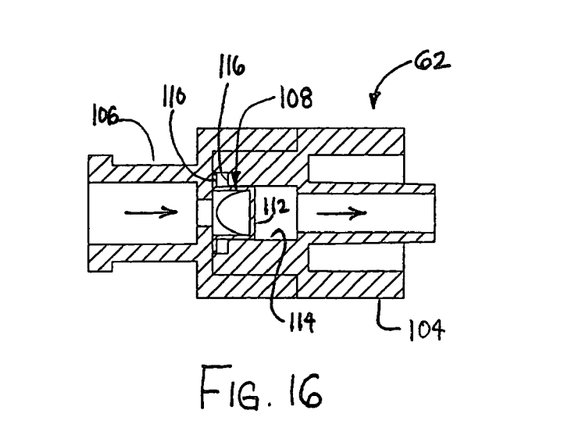
FIG. 16 is an assembled cross-sectional view of the check valve of FIG. 14.

Referring to FIGS. 14-16, an embodiment of first check valve 62 is shown. In the illustrated embodiment, first check valve 62 includes a first body portion 104, a second body portion 106 and a valve member 108. In a particular implementation, valve member 108 is a well known duckbill-style valve made of medical grade rubber or other resiliently flexible polymer. In the illustrated configuration, valve member 108 includes a flange 110 and a mouth 112 that is normally closed, but opens at a predetermined fluid pressure, commonly referred to as the "cracking pressure", to allow passage of the fluid. The cracking pressure may be tailored to a particular biopsy system application by modifying, among other features, the dimensions of mouth 112 and the flexibility of the valve member material.

Valve member 108 is received in an opening 114 in first body portion 104, with flange 110 being received in a chamfer 116. Second body portion 106 is secured to first body portion 104 by a pair of mating threads (not shown), by gluing the components together or by any other suitable method. Once first check valve 62 is assembled, valve member 108 is positioned such that mouth 112 is downstream of flange 110. This configuration allows a fluid to flow through valve member 108 in the direction of the arrows shown in FIG. 16, but prevents the fluid from flowing in the opposite direction.

In the illustrated embodiment, first body portion 104 includes a male luer fitting adapted to mate with a corresponding female luer fitting on first inlet port 68 of body member 60. Similarly, second body portion 106 includes a female luer fitting adapted to mate with a male luer fitting on the upstream fluid conduit section 26A. While a luer style fitting configuration allows the components to be easily connected and provides a fluid-tight seal, other fitting styles and configurations are also within the scope of the present invention.

In a biopsy procedure, opening 40 in outer cannula 30 is positioned adjacent a tissue mass using an imaging system, such as MRI. Inner cannula 36 is then reciprocatingly moved to successively remove pieces of the target mass while the excised tissue is continuously drawn into the collection trap 48 by the aspiration pressure or vacuum in inner lumen 44. During each stroke of inner cannula 36, the vacuum used to draw the biopsy sample through inner cannula 36 will also draw a predetermined amount of fluid from fluid source 24 into the area surrounding opening 40, provided inner cannula 36 is not abutting cutting board 42. Particularly, the aspiration pressure or vacuum will overcome the cracking pressure of first check valve 62, allowing a predetermined amount of fluid to be drawn into outer cannula 30 during each stroke. In a particular implementation, about 1-2 cc of fluid passes through first check valve 62 during each stroke of inner cannula 36.

If second fluid source 65 is connected to second check valve 64, valve member 82 will be compressed such that the aspiration pressure or vacuum will automatically draw a predetermined amount of fluid, such as an anesthetic or a haemostatic agent, from second fluid source 65 with every stroke of inner cannula 36. In a particular implementation of the invention, second check valve 64 is configured to allow about 1 cc of fluid into fluid connector 22 during each stroke of inner cannula 36.

Of course, additional fluid contained within second fluid source 65 may be forced into fluid connector 28 at any time, particularly when second fluid source 65 functions as a syringe. However, because fluid may be automatically drawn from second fluid source 65, there is generally no need to physically inject a second fluid into fluid connector 22, which shortens the procedure time. Provided fluid is being drawn from second fluid source 65, the aspiration pressure or vacuum in fluid connector 28 may be lower than the cracking pressure of valve member 108, and little or no fluid will be drawn from first fluid source 24. Valve 108 also prevents fluid back-flow into fluid conduit section 26A of the fluid being introduced from second fluid source 65 into connector 28. However, when second fluid source 65 is empty, the aspiration pressure or vacuum in fluid connector 28 will exceed the cracking pressure of valve member 108 and fluid will be drawn from first fluid source 24.

It will be appreciated that biopsy system 20 of the present invention is a completely "closed" tissue excision and recovery system. Unlike some prior art biopsy systems, the fluid delivery portion of biopsy system 20 is fluid tight so that no bodily fluids can escape. Moreover, biopsy system 20 does not require that fluid supply line 26 be "broken" to introduce two or more fluids to the biopsy site.

The present invention has been particularly shown and described with reference to the foregoing embodiments, which are merely illustrative of the best modes for carrying out the invention. It should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

What is claimed is:

1. A fluid connector for a biopsy system including a vacuum assisted biopsy device, comprising:
 a unitary body member defined by a first channel and a second channel, wherein the second channel is integrally connected directly to the first channel; and wherein the first channel is defined by a first inlet port and an outlet port, and wherein the second channel is defined by a second inlet port and a distal end, and wherein the distal end intersects the first channel; and wherein the first channel includes a first check valve; and wherein the second channel includes a second check valve, and the outlet port is in communication with the biopsy device, and wherein the first check valve is configured to automatically open when a vacuum is introduced through the biopsy device and to the fluid connector, and wherein the second check valve is configured to be selectively opened.

2. The fluid connector of claim 1, wherein the first check valve includes a duckbill valve member.

3. The fluid connector of claim 1, wherein the second check valve includes a resiliently compressible valve member.

4. The fluid connector of claim 3, wherein the second check valve includes a valve seat adapted to secure the valve member within the second check valve.

5. The fluid connector of claim 1, wherein the outlet port is configured as a male luer fitting.

6. The fluid connector of claim 5, wherein the male luer fitting further comprises a flanged tubular portion and an internally threaded cap.

7. The fluid connector of claim 1, wherein the second check valve further comprises first and second body portions, a flexible valve member, and a valve seat, wherein the second body portion is at least partially received within the first body portion and the valve member are retained within the second body portion by the valve seat.

8. The fluid connector of claim 7, wherein the valve member includes a base that comprises a plurality of fins that are configured to engage an inner wall of the second body portion.

9. A biopsy system, comprising:
a vacuum assisted biopsy device comprising an outer cannula and an inner cannula,
a fluid connector positioned remotely from the biopsy device,
wherein the fluid connector comprises a body member defined by a first channel and a second channel, the second channel intersecting the first channel;
wherein the first channel includes a first inlet port and an outlet port, the inlet port configured to be operatively connected to a first fluid source and the outlet port configured to be operatively connected to the biopsy device;
wherein the first channel further includes a first check valve in fluid communication with the first inlet port;
wherein the second channel includes a second inlet port and a distal end, wherein the second inlet port is configured to be operatively connected to a second fluid source,
wherein the second channel further includes a second check valve;
wherein the first check valve is configured to open and automatically pass the first fluid from the first fluid source in response to a vacuum from a vacuum source coupled to a proximal end of the inner cannula causing the first fluid to be delivered into the outer cannula; and
wherein the second check valve is configured to be opened and pass the second fluid to be delivered into the outer cannula.

10. The fluid connector of claim 9, wherein the first fluid source is a bag of isotonic solution.

11. The biopsy system of claim 9, wherein the second fluid source includes a needleless syringe.

12. The biopsy system of claim 9, wherein the second fluid source includes an anesthetic or a haemostatic agent.

13. The biopsy system of claim 9, wherein the cracking pressure is less than or equal to a pressure resulting from the vacuum delivered through the vacuum assisted biopsy device.

14. The biopsy system of claim 13, wherein the cracking pressure is greater than a pressure resulting from the vacuum created in the fluid connector by the vacuum assisted biopsy device when the second check valve is open.

15. The biopsy system of claim 9, wherein the second check valve includes a female luer fitting and the second fluid source includes a male luer fitting adapted to mate with the female luer fitting.

16. The biopsy system of claim 9, wherein the fluid connector is configured to pass the second fluid from the second fluid source and through the output port and into the biopsy device in response to the vacuum when a syringe is fluidly connected to the fluid connector.

17. The biopsy system of claim 9, wherein one of the first and second check valves each include a female luer fitting.

18. The biopsy system of claim 9, wherein the vacuum assisted biopsy device further comprises a hub that supports the outer cannula, wherein the hub is connected to a first end of a fluid conduit and a second end of the fluid conduit is attached to the outlet port of the fluid connector so as to introduce fluid into the outer cannula.

19. The biopsy system of claim 18, wherein the first and second fluid sources are connected to the first and second inlet ports, respectively, by separate fluid conduits.

20. The biopsy system of claim 9, wherein a fluid conduit connects the fluid connector to the vacuum assisted biopsy device.

21. The fluid connector of claim 9, wherein each of the female luer fittings include a threaded surface.

22. The biopsy system of claim 9, wherein the inner cannula is configured for a reciprocating cutting stroke within the outer cannula and wherein during each stroke, the vacuum draws a predetermined amount of the first fluid into the biopsy device.

23. The biopsy system of claim 22, wherein the vacuum is configured to overcome a cracking pressure of the first check valve to pass the first fluid into the outer cannula during each stroke.

* * * * *